United States Patent [19]

Farley et al.

[11] Patent Number: 5,624,457
[45] Date of Patent: Apr. 29, 1997

[54] DIRECTIONAL ATHERECTOMY DEVICE WITH FLEXIBLE HOUSING

[75] Inventors: Brian Farley, Los Altos; Anthony J. Castro, San Francisco, both of Calif.

[73] Assignee: Devices for Vascular Intervention, Santa Clara, Calif.

[21] Appl. No.: 224,169

[22] Filed: Apr. 7, 1994

[51] Int. Cl.$^6$ .................................................. A61B 17/32
[52] U.S. Cl. .................... 606/170; 606/159; 606/171; 606/180
[58] Field of Search ...................... 606/159, 171, 606/170, 180; 128/753, 754

[56] References Cited

U.S. PATENT DOCUMENTS

| | | | |
|---|---|---|---|
| 4,950,277 | 8/1990 | Farr | 606/159 |
| 4,986,807 | 1/1991 | Farr | 606/159 X |
| 5,222,966 | 6/1993 | Perkins et al. | 606/159 |
| 5,224,949 | 7/1993 | Gomringer et al. | 606/159 |
| 5,312,425 | 5/1994 | Evans et al. | 606/159 |

Primary Examiner—Angela D. Sykes
Assistant Examiner—Michael Peffley
Attorney, Agent, or Firm—Douglas A. Chaikin, Esq.; Peninsula IP Group

[57] ABSTRACT

An intravascular directional atherectomy device is disclosed. The apparatus comprises a catheter body having a distal end, a proximal end and an axial lumen therebetween. A housing having an open interior and an aperture on a lateral side thereof is attached to the distal end of the catheter body. An atheroma severing device is disposed within the housing. The device includes a cutter that is slidably disposed on a saddle which is connected to the housing. A track member is disposed in the axial lumen of the catheter body and has a distal end connected to the housing. Slidable movement of the atheroma severing device severs the stenotic material that has been urged within the aperture. The saddle enables the inflexible portion of the housing to be minimized in order to fit in the very tortious regions of biological conduits.

2 Claims, 3 Drawing Sheets

DIRECTIONAL ATHERECTOMY DEVICE WITH FLEXIBLE HOUSING

RELATED APPLICATIONS

This application contains subject matter related to that in the following applications which are being filed on the same day as this application: U.S. Ser. No. 08/363,142, now allowed, U.S. Ser. No. 08/236,485 now U.S. Pat. No. 5,507,795; and Ser. No. 08/357,999, now allowed. The full disclosure of each of these applications is incorporated herein by reference.

BACKGROUND OF THE INVENTION

1. Field of Invention

The present invention relates generally to the construction and use of vascular and other catheters. More particularly, the invention relates to atherectomy catheters for treating stenotic vasculature having an atheroma severing device at their distal ends.

2. Previous Art

Arteriosclerosis, also known as atherosclerosis, is a common human ailment arising from the deposition of fatty-like substances, referred to as atheroma or plaque, on the walls of blood vessels of biological conduits. Some stenotic regions also contain hard calcified deposits. Stenotic deposits occur both in peripheral blood vessels that feed the limbs of the body and coronary blood vessels which feed the heart. When deposits accumulate in localized regions of an individual's blood vessel, blood flow is restricted and that person's health is at serious risk.

Numerous approaches for reducing and removing such vascular deposits have been proposed, including balloon angioplasty, where a balloon-tipped catheter is used to dilate a region of atheroma; atherectomy, where a blade or other cutting element is used to sever and remove the atheroma; stent insertion, where a liner is placed and expanded at the site of the blockage; and laser angioplasty where laser energy is used to ablate at least a portion of the atheroma. Of particular interest to the present invention are atherectomy devices and methods where an atheroma severing device is advanced past an opening in a housing at the distal end of a vascular catheter. By positioning the housing so that at least a portion of the atheroma passes through the opening, the atheroma can be severed by advancing the atheroma severing device. Typically, such atheroma severing devices are circular cutting blades which are rotated and advanced simultaneously to effect the desired cutting.

U.S. Pat. No. 4,669,469 and European patent application EPA 163 502, each illustrate exemplary atherectomy devices of the type described above, where the cutter housing is typically a rigid metal cylinder. Rigid cutter housings, however, are problematic when the catheters are being used in small, tortuous blood vessels where the catheter tip must pass through curves having small diameters. Moreover, difficulties have been encountered in containing the circular cutting blade within the housing. It has generally been necessary to limit the area of the opening in the housing in order to assure containment and smooth travel of the blade. Such an approach is disadvantageous, however, since it limits exposure of the blade to the atheroma and the amount of atheroma which may be severed in a single pass of the blade.

To overcome the limitations inherent in rigid housing designs, the use of flexible cutter housings has been proposed. U.S. Pat. No. 4,781,186, describing the construction of atherectomy catheters having flexible cutter housings which may comprise a slotted metal or metal braid configuration. While the use of flexible housings provides an improvement in the ability to position the distal end of the catheter within tortuous portions of the vascular system, such flexible housings exacerbate the problems with guiding the atheroma severing device within the housing. The ability to traverse the more tortuous blood vessels is related to the length of the inflexible section of the device, or the length of the least flexible portion of the cutter. What is needed is an atherectomy device that can at once be navigated through tortuous portions of the vascular system and provide for smooth guidance of the atheroma severing device within its housing.

SUMMARY OF THE INVENTION

It is a general object of this invention to provide an atherectomy device which minimizes the inflexible length of the catheter to facilitate passing a catheter in small tortuous regions of the biological conduits.

It is another object of this invention to provide such a catheter device which may be used with flexible and inflexible catheter housings.

It is an additional object of this invention to provide such an atherectomy device which includes a guide mechanism for the atheroma severing device, including a path defining member for a cutter.

In accordance with the above objects and those that will be mentioned and will become apparent below, an atherectomy device comprising:

a catheter body having at least one lumen extending between its proximal and distal ends, the catheter body having a longitudinal axis;

a housing connected to the distal end of the catheter body, the housing having an open interior and an aperture elongated along the longitudinal axis;

an atherectomy severing device disposed within the housing comprising a cutter for removing atheroma, a saddle for retaining the cutter device, and a retainer for retaining the saddle within the housing and adapted for connection with the housing, whereby the atheroma severing device is retained within the housing while in operation.

In an exemplary embodiment, the retainer includes a keeper connected to the saddle and a rod member connected to the housing. The keeper is slidably connected to the rod member and allows the atheroma severing device to slide within the housing past aperture for removal of arethoma.

In another exemplary embodiment, the retainer includes a path defining member connected to the housing. The path defining member defines a track running along the longitudinal axis of the catheter body. The retainer additionally includes a keeper element connected to the saddle for connecting the saddle to the path defining member. The connection is a slidable one in which the atheroma severing device can be slid between the distal and proximal ends of the housing along the aperture as desired as the atheroma severing device removes atheroma.

In another exemplary embodiment, the keeper element has a single slot which matches and is compatible with the path defining member having a compatible slotted member.

In an additional exemplary embodiment the keeper element comprises a plurality of slots for compatible sliding with a compatible plurality of path defining members.

In an additional embodiment, the proximal end of the housing extends over the distal end of the catheter body for connection to an exterior surface of the catheter body. In this embodiment, the proximal end of the housing is flared or swaged to provide an enlarged interior diameter for receiving the distal end of the catheter body.

In another exemplary embodiment, the distal end of the catheter body will extend over the proximal end of the housing for connection to an exterior surface of the housing. In this embodiment, the connection means includes a ring disposed over the distal end of the catheter body for compressing the catheter body against the housing. The housing contains the saddle disposed within the housing to contain an atheroma severing device for removing atheroma. Where the atheroma severing device includes a cutter, the cutter is disposed on the saddle.

In another exemplary embodiment, the catheter includes structure for limiting the travel of the cutter. The travel limit is connected to the drive cable. Additionally, the distal end of the housing includes a parting surface. The path defining member is fixed relative to the housing along the longitudinal axis.

The keeper element allows axial reciprocation of the saddle along the path defining member. The path defining member guides the saddle adjacent the aperture of the housing effectively eliminating protrusion of the cutter through the aperture, even when the atheroma severing device is advanced through a significant bend or deformed flexible housing. The retainer also prevents escape of the saddle and device even upon extreme flexion of the catheter, catheter body and housing. In this embodiment, the catheter is positioned within a biological conduit with the aperture positioned over the stenotic material. A balloon on the side opposite to the aperture is inflated to force the stenotic material into the aperture. The drive cable is activated so as to rotate the cutter as it is translated axially to sever the stenotic material against the parting surface. Travel of the cutter in the saddle toward the proximal end of the housing is limited by the travel limit. As the drive shaft is moved toward the distal end, the travel limit and cutter are advanced thereby toward the distal end of the housing. As the travel limit advances it contacts the saddle and moves the saddle along the track with the cutter.

In this manner, the flexure limiting, rigid portion of the catheter corresponds to the saddle length, which is only slightly longer than the cutter itself. The remainder of the catheter may be constructed of truly flexible components and thus access small and tortuous blood vessels not easily treated heretofore. Such catheter designs should be compatible with the use of flexible distal housings, including, but not limited to, polymeric housings, flexible metal housings, and the flexible housing designs which might be employed.

In another exemplary embodiment, the atheroma severing device comprises a cutter slidably disposed within the housing. The cutter is connected at its proximal end to the distal end of a drive cable. The drive cable is connected at its proximal end to a drive mechanism including a means for coupling its proximal end to a drive motor. Preferably, the cutter is rotatable. Stenotic material is severed by axially translating the rotating cutter across the aperture by means of the drive cable. The material is then stored in the nose cone.

It will be appreciated that the above may apply equally whether the housing is flexible or rigid.

It is an advantage of this invention to provide a directional atherectomy device having a flexible cutter which is capable of treating small tortuous vessels.

It is an additional advantage of the atherectomy device in accordance with this invention to provide a flexible catheter housing and a rigid saddle minimizing the overall rigid area of the catheter body.

It is an additional advantage of the atherectomy device in accordance with this invention, to provide such a device which is readily adapted to either a conventional flexible or rigid housing to minimize housing length.

DETAILED DESCRIPTION OF THE INVENTION

The present invention is useful with a wide variety of catheters having virtually any type of atheroma severing device. The present invention may be used with a rotating or reciprocating cutting blade which is simultaneously rotated or reciprocated and axially advanced past a side aperture in a cutter housing in a known manner. Such atherectomy devices and procedures are described in U.S. Pat. Nos. 4,669,469; 4,926,858; 4,979,951; 5,047,040; 5,084,010; Reissue Pat. No. 33,569, and co-pending application U.S. Ser. No. 08/236,485, Attorney Docket Number DEVI1464, entitled "Catheter With Perfusion System", and co-pending application U.S. Ser. No. 08/363,142, Attorney Docket number DEVI1456, entitled "Universal Catheter With Interchangeable Work Element", the full disclosures of which are incorporated herein by reference. The remaining disclosure will be directed particularly at the incorporation of directional atheroma severing device of the present invention in such atherectomy catheters. It is to be understood, however, that the principles of the present invention can be applied to many other catheter types.

Figure 1:
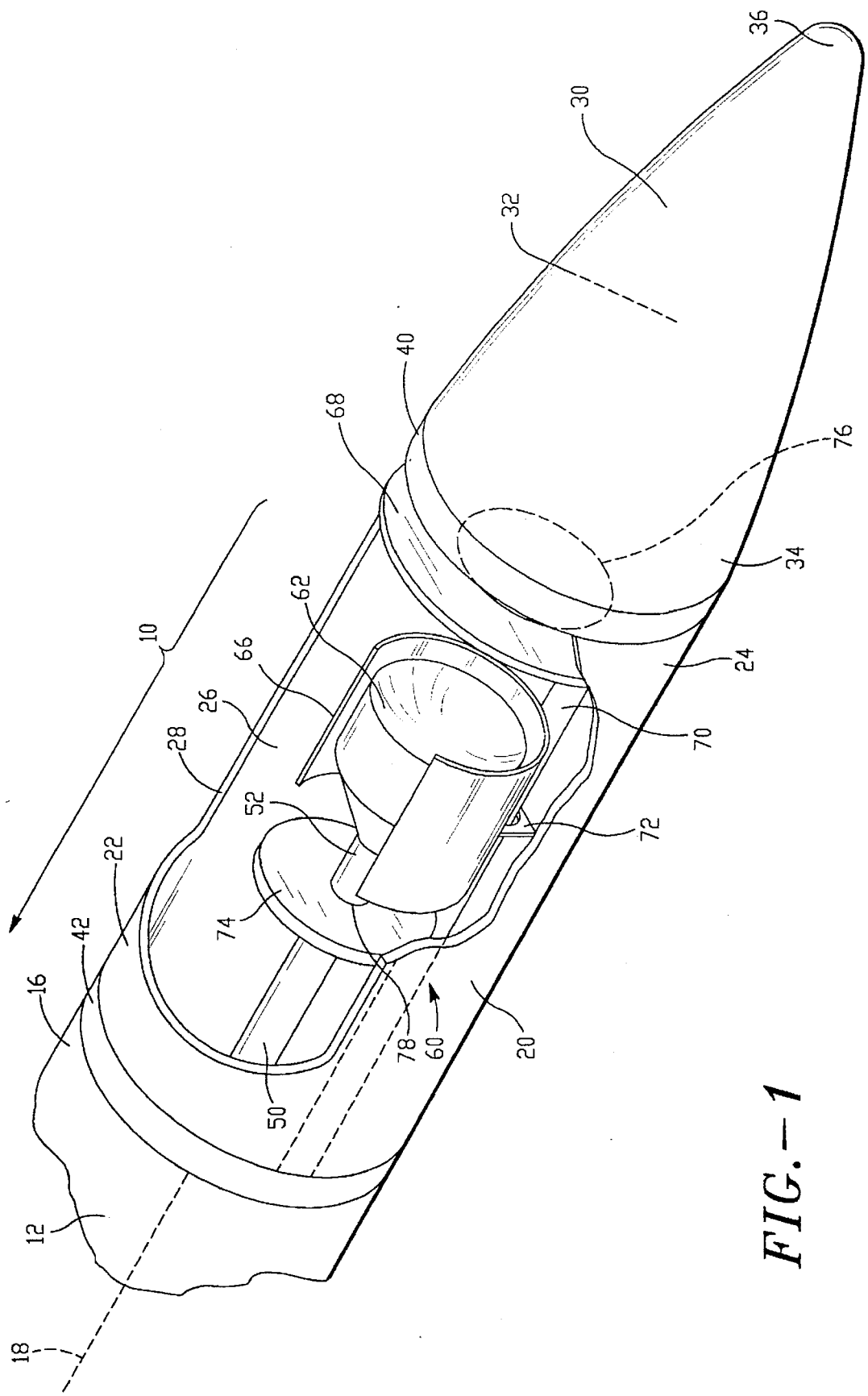
FIG. 1 is a perspective view of the atherectomy device in accordance with this invention.

With respect to FIG. 1 there is shown the atherectomy catheter in accordance with this invention generally denoted by the numeral 10. The atherectomy catheter 10 includes a catheter body 12. The catheter body 12 has a proximal end (not shown) and a distal end 16. The catheter body 12 has a longitudinal axis 18 extending from the proximal end to the distal end 16.

The atherectomy catheter 10 includes a catheter housing 20. Likewise the housing 20 has a proximal end 22 and a distal end 24. The housing 20 is connected at the distal end 16 of the catheter body 12 as clearly shown in FIG. 1.

The housing has an open interior 26 aligned with the interior opening of the catheter body (not shown). Thus, when connected, the catheter body 12 and the catheter housing 20 create a flow through interior as clearly shown throughout the figures. The catheter housing 20 has a aperture 28. The aperture 28 is elongated along the longitudinal axis 18.

The atherectomy catheter 10 includes a nose cone 30 with a distal end 36 and a proximal end 34. The nose cone 30 is attached to the catheter body as shown in FIG. 1. As is well known in the art, the nose cone 30 is used for receiving stenotic material. The nose cone 30 includes a central interior opening 32 for receiving the stenotic material.

The nose cone 30 is connected to the housing 20 via a connecting member 40 and the housing 20 is connected to the catheter body 12 via a connecting member 40. There are several alternative methods of securing the nose cone 30, housing 20 and catheter body 12.

One alternative is that the distal end 16 of the catheter body 12 may extend over the proximal end 22 of the housing 20 for connection with an exterior surface of the housing. In a similar fashion, the nose cone 30 may extend over the distal end 24 of the housing 20. The catheter body 12 and/or the nose cone 30 may then be welded or bonded to the housing 20. Alternatively, the catheter body 12 and nose cone 30 may be connected to the housing 20 using rings disposed over the distal end 16 of the catheter body 12 and the proximal end 34 of the nose cone 30. The rings compress the catheter body and nose cone against the housing by shrinking or crimping. In an additional alternate embodiment, the proximal end 22 of the housing 20 may extend over the distal end 16 of the catheter body 12 and be secured by welding, bonding or compression of the connecting members 40 and 42. Like alternatives exist for connecting the housing 20 and nose cone 30.

Disposed within the interiors of the catheter body 12 and housing 20 is an axial drive cable or drive shaft 50 which is both rotatable and reciprocal therein. The drive shaft 50 has a proximal end (not shown) connected to a motor drive unit (not shown) which causes the drive shaft 50 to rotate when activated. Additionally, the drive shaft 50 is of sufficient length that it can be maneuvered reciprocally within the interiors of the catheter body 12 and the housing 20. The drive shaft 50 has distal end 52. Connected to the distal end 52 of the drive shaft 50 is an atheroma severing device generally indicated by the numeral 60 (shown particularly in FIG. 2). The atheroma severing device 60 comprises a cutter 62 connected to the distal end 52 of the drive shaft 50.

Additionally, the atheroma severing device 60 includes a track member 70 disposed axially and in general alignment with the longitudinal axis 18. The atheroma severing device 60 includes a saddle 66. At the distal end of track member 70 and adjacent the nose cone 30 is disposed a parting surface 68 which includes a central opening 76 permitting communication between the interior 26 of the housing 20 and the interior 32 of the nose cone 30. The atheroma severing device 60 includes a travel limit 74 which is connected to the track member 70 for limiting the retrograde axial motion or travel of the cutter 62. The saddle 66 includes a keeper element 72 for maintaining the saddle 66 on the track member 70.

The atheroma severing device 60 is positioned adjacent the elongated aperture 28 also known as a catheter window by those ordinarily skilled in the art. Thus, as the cutter 62 is operationally reciprocated across the aperture 28 for cutting and removing stenotic material, the saddle 66 moves with the cutter 62 in a similar fashion.

The saddle 66 is constructed from material rigid enough to withstand the axial and rotational translational forces of the atheroma severing device 60. Suitable material for manufacturing the saddle 66 include stainless steel, nickel titanium alloys and the like. Polymeric materials, such as polyacetals, polycarbonates, polyurethanes and the like, may be used to form the saddle 66 as well.

The catheter body 12 is elongated over its longitudinal axis 18. The catheter body 12 is made from a flexible tube having a proximal end (not shown) and a distal end 16. There exists at least one lumen between the proximal and distal defining an interior opening.

The term "catheter body" defines a flexible tube and, in a preferred embodiment, is formed by impregnating braided metal tubes with a supporting material such as nylon polymer blends as described in pending application Ser. No. 08/089,954, filed 9 Jul. 1993 and assigned to the same assignee as the instant invention. The disclosure of this invention is specifically incorporated herein. The reinforced catheter is desirable when torquing is used in the operating procedure for positioning of the housing 20.

The catheter body 12 has a length along its longitudinal axis 18 from about 40 cm to about 200 cm. Of course, it will be appreciated that shorter catheters from about 40 cm to 120 cm are within the scope of this invention. Such shorter catheter bodies 12 may be used for peripheral applications, while longer catheters (in the range of from about 100 cm to 200 cm) are used for coronary applications. The diameter of catheter body 12 may also vary, with smaller diameter catheters in the range being from about 3 French (1 F=0.33 mm) to 6 French for coronary applications, and a diameter from 3 French to 11 French for peripheral applications.

The housing 20 is made from a flexible material such as an organic polymer such as nitinol, nylon or polyurethane. It is preferable that the housing 20 be resilient to facilitate bending. The construction of flexible housing is illustrated in U.S. Pat. No. 4,781,186 and co-pending application Ser. No. 07/726,626, the disclosures of which are specifically incorporated herein by reference.

Alternatively, the housing may be made from a rigid material, such as metal, for example, surgical stainless steel. In order to promote the maximum amount of flexibility, spaces, slots or voids can be incorporated into the housing when it is constructed of metal.

In either alternative, the housing 20 has a flexibility not heretofore possible because of the use of the rigid saddle 66. This enables the length of rigid portion of the catheter body 12 and housing 20 to be diminished to a length approaching the length of the cutter 62 itself. Optimizing the flexibility in this way allows the catheter 10 to be able to fit through the tortuous and narrow passageway of the biological conduit.

The length of the housing 20 may be varied as desired. Typically, if large amounts of stenotic material are to be severed, the housing 20 will be longer. It will be appreciated that if the housing 20 is longer, it is more difficult to manipulate the catheter through the vascular system and, particularly now, the biological conduits. Typically, the length of the housing 20 will be from 5 mm to 40 mm. For coronary applications, the length of the housing 20 will generally be shorter, in the range of about 8 mm to 17 mm. The housing diameter 20 corresponds to the diameter of the catheter body 12, again in the range of from about 3 French to 11 French.

Aperture 28 extends over at least one half of the housing 20. In some preferred embodiments, the aperture 28 length extends over approximately three-quarter's of the housing 20 length. It is, of course, desirable to remove as much stenotic material as possible in a single pass of the cutter 62. However, this desire is limited by the loss of flexibility of the length of the housing.

In use, the proximal end of the drive shaft 50 is connected to a motor drive unit and of sufficient length to allow an operator to not only rotate the drive shaft 50, but also to reciprocate the drive shaft 50 by sliding it back and forth along the longitudinal axis 18. As set forth earlier, the atheroma severing device 60 comprising a retainer is reciprocated along track 70 and kept connected to the track 70 by keeper element 72. As can be seen from FIG. 1 the saddle 66 acts as a guide for the cutter 62 keeping the cutter moving along the longitudinal direction while, at the same time, preventing the cutter from being released out of the aperture 28. As the stenotic material is cut by cutter 62 it is captured within the open interior 26 of the housing 20. The cutter is reciprocated toward the distal end 24 of the housing 20 for abutting contact with the parting member 68. The parting member 68 includes a central opening 76 which is aligned with the central opening 32 of the nose cone 30. The stenotic material is pushed into the nose cone by the reciprocating stroke of the drive shaft 50. The stroke continues toward the distal end until it is limited in its travel by parting member 68.

Figure 2:
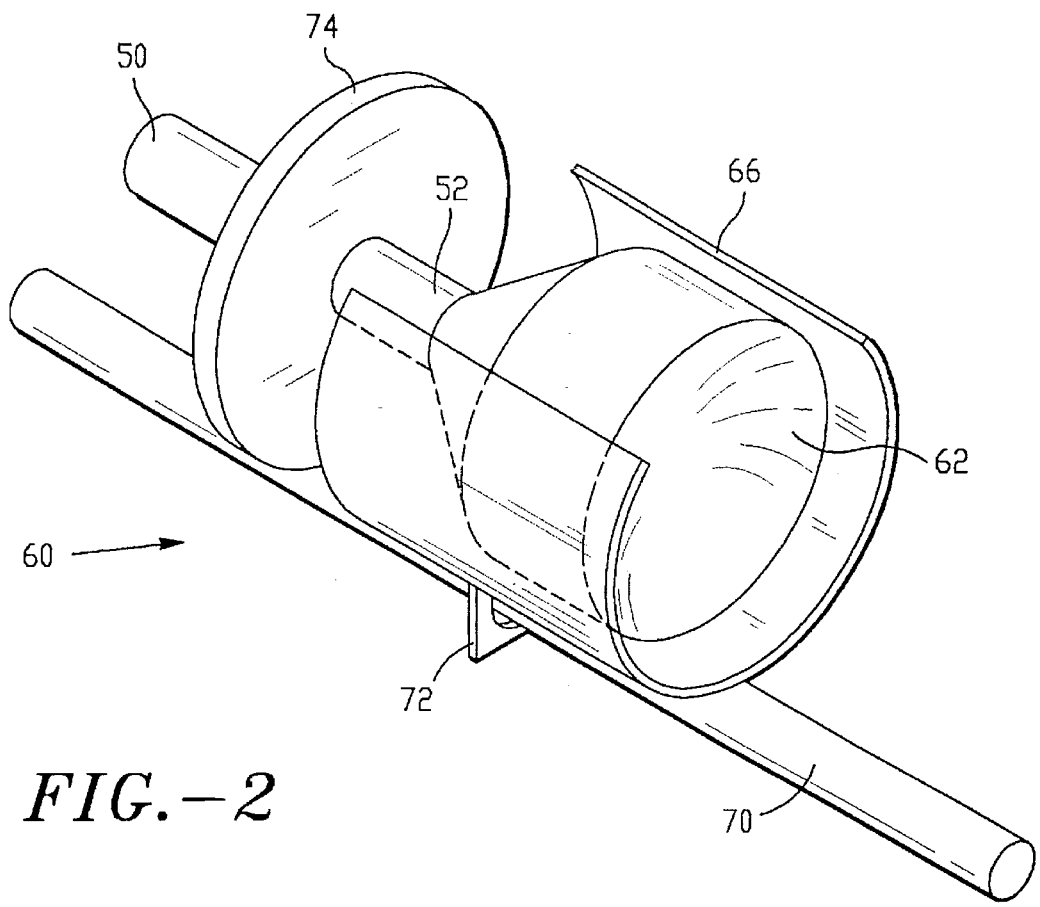
FIG. 2 is an enlarged perspective view of the atherectomy device shown in FIG. 1 illustrating the rod track embodiment.

With respect to FIG. 2 there is shown an enlarged view of the atheroma severing device generally indicated by the numeral 60. As set forth earlier, the retainer is appended to the saddle 66 and has a keeper element 72. The keeper 72 is a tab attached to the saddle 66 and encircling the track 70. The keeper 72 retains the saddle for reciprocal motion along the track 70 as illustrated in FIG. 2. The atheroma severing device 60 includes a single rod member 70 in the embodiment shown in FIG. 2 and a single keeper element 72 having a central opening for slidable connection with the track 70.

The retrograde travel of the axially reciprocating stroke is limited by a travel limit 74 of the interior diameter of the housing 20. The travel limit has an opening 78 located centrally through which the drive shaft 50 freely passes. The travel limit 74 is attached to the track 70 and acts as a stop preventing the work element from retracting further.

As described, the travel limit 74 works in conjunction with the saddle as part of the severing device 60, and moves the saddle 66 along. It is also clear from FIGS. 1 through 6 that the travel limit 74 works in conjunction with the saddle as part of the severing device 60.

The track member 70 is a flexible rod disposed coaxially with the drive shaft 50 within the housing 20. As shown in FIG. 1, the track member 70 is attached to the parting member 68 for connection to the housing 20. The track member 70 is made from biologically compatible materials such as stainless steel.

Figure 3:
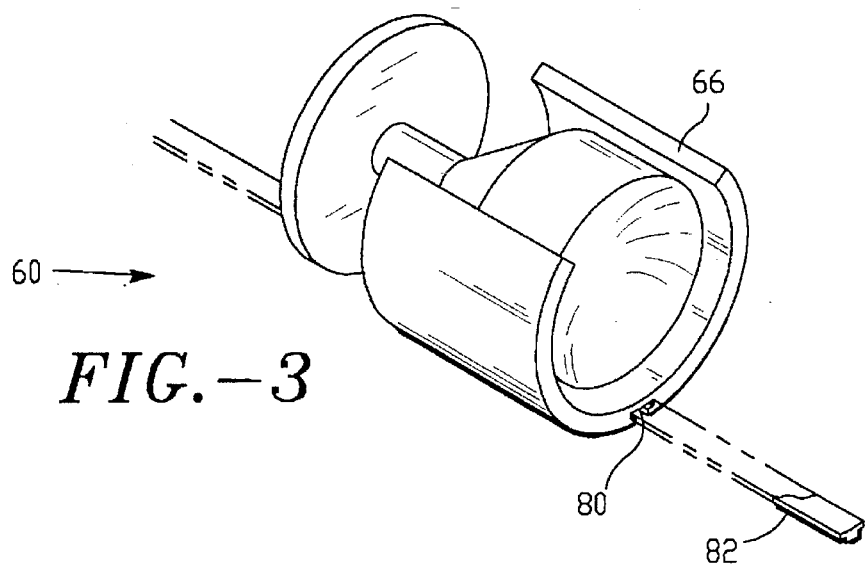
FIG. 3 is a perspective view of another embodiment of the atherectomy catheter device in accordance with this invention illustrating another embodiment of the retainer.

With particular reference to FIG. 3, there is shown another embodiment of the atheroma severing device 60. It will be seen that the retainer is an integral part of the saddle 66 and has a keeper element comprising a single slot 80 in the outer surface of the saddle 66. The device 60 of FIG. 3 includes a track member 82 sized and shaped for compatible sliding engagement with the slot 80. The slot 80 enables the saddle 66 to be reciprocated along the track member 82 as with the earlier described embodiments of FIGS. 1 and 2.

Figure 4:
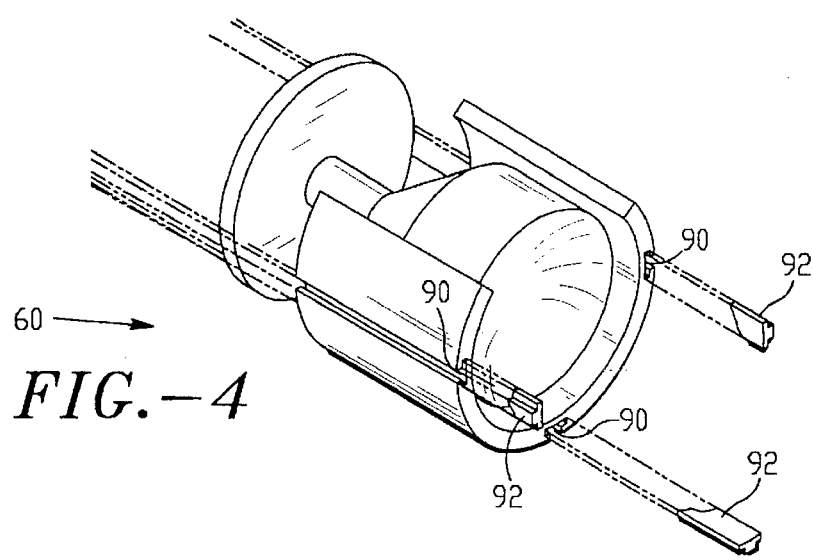
FIGS. 4, 5 and 6 illustrate additional embodiments of the retainer for atherectomy catheter device in accordance with this invention.

With particular respect to FIG. 4, there is shown an alternative embodiment of the atheroma severing device 60. As illustrated, the retainer comprises a three-slotted keeper element 90. As will be appreciated, each slot of the keeper element 90 is identical to the keeper element 80 of FIG. 3. Likewise, there are three track members 92 in the embodiment of FIG. 4. The operation of keeper element 90 and track member 92 is similar to that described above with respect to FIG. 3.

Figure 5:
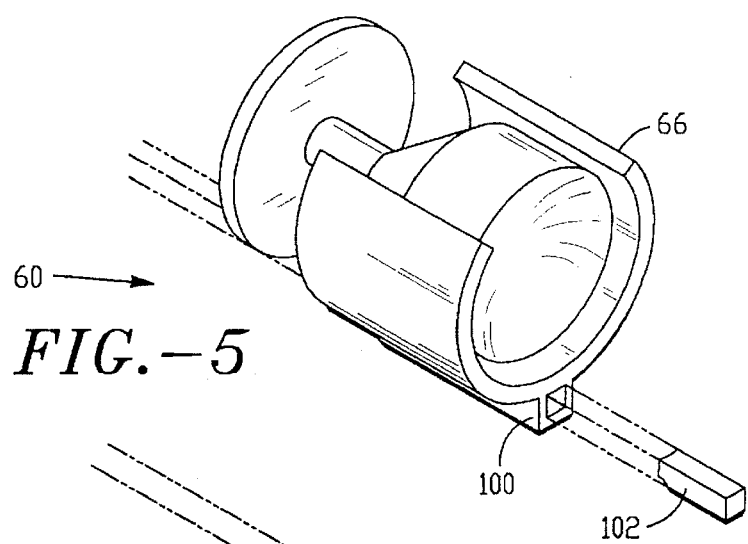

With respect to FIG. 5, there is shown another embodiment of the atheroma severing device 60. In this embodiment, the keeper element 100 comprises a single holed element and a track member 102. While it can be seen that the keeper element 100 and track member 102 are in a generally elongated rectangular shape, it will be appreciated that other configurations of these elements of the invention are also possible within the spirit and scope if this invention.

Figure 6:
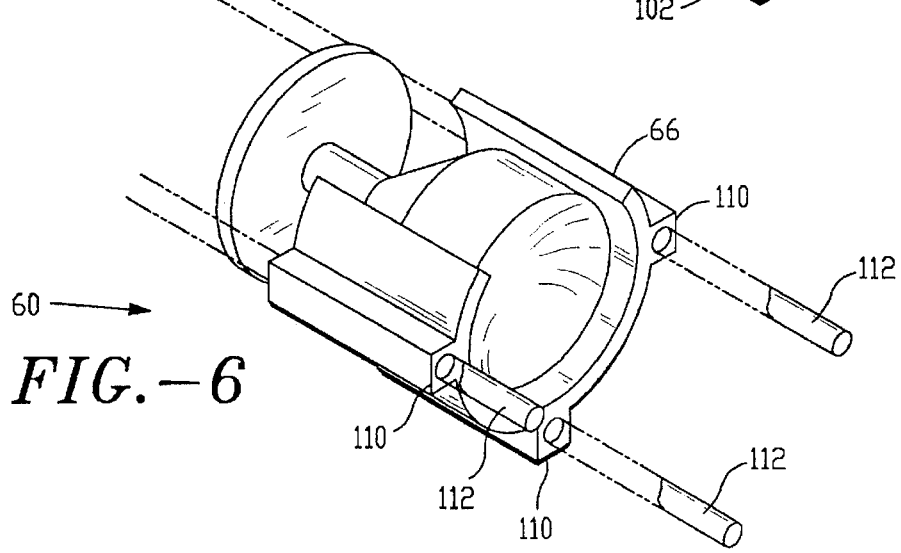

Similarly, with respect to FIG. 6, there is shown another embodiment of the atheroma severing device 60 in accordance with this invention. In this embodiment the keeper element 110 comprises a three-holed element and three compatible rail elements 112. Similar to the embodiment shown in FIG. 5, the geometric configuration of the keeper element 110 and track member 112 may be varied within the spirit and scope of this invention element.

While the foregoing detailed description has described embodiments of the atherectomy device in accordance with this invention, it is to be understood that the above description is illustrative only and not limiting of the disclosed invention. Particularly, the invention may have either a flexible or a rigid housing within the spirit and scope of the invention. It will be appreciated that, also within the spirit and scope of this invention, the device may be adaptable to a variety of different catheter bodies or a variety of different catheters designed for engagement and intervention in biological conduits. Thus, the invention is to be limited only by the Claims as set forth below.

What is claimed is:

1. An atherectomy catheter device for severing atheroma, comprising:

a catheter body having a proximal end, a distal end, and a longitudinal axis which extends therebetween;

a housing connected to the distal end of the catheter body, the housing having an open interior and an aperture;

a cutter having an arcuate edge disposed within the housing, the cutter rotates and reciprocates along the longitudinal axis to sever atheroma;

a saddle surrounding a portion of the cutter to retain the cutter within the housing;

a retainer for connecting the saddle and the housing to enable the cutter to reciprocate within the housing, the retainer includes first and second rods within the housing and a keeper member slidably connected to the first and second rods, the keeper member retains the saddle in alignment with the longitudinal axis.

2. An apparatus as set forth in claim 1, wherein the the keeper member includes tabs which slidably encircle the first and second rods.

* * * * *